United States Patent
Birkhold et al.

(10) Patent No.: US 11,200,463 B2
(45) Date of Patent: Dec. 14, 2021

(54) METHOD FOR ADAPTING AN IMAGE IMPRESSION

(71) Applicant: Siemens Healthcare GmbH, Erlangen (DE)

(72) Inventors: Annette Birkhold, Nuremberg (DE); Christian Kaethner, Forchheim (DE); Markus Kowarschik, Nuremberg (DE)

(73) Assignee: Siemens Healthcare GmbH, Erlangen (DE)

( * ) Notice: Subject to any disclaimer, the term of this patent is extended or adjusted under 35 U.S.C. 154(b) by 245 days.

(21) Appl. No.: 16/597,520

(22) Filed: Oct. 9, 2019

(65) Prior Publication Data
US 2020/0117957 A1    Apr. 16, 2020

(30) Foreign Application Priority Data
Oct. 11, 2018 (EP) .................................. 18199877

(51) Int. Cl.
*G06K 9/00* (2006.01)
*G06K 9/62* (2006.01)
(Continued)

(52) U.S. Cl.
CPC ........... *G06K 9/6267* (2013.01); *G06N 20/00* (2019.01); *G06T 11/003* (2013.01); *G16H 30/40* (2018.01); *G06T 2210/41* (2013.01)

(58) Field of Classification Search
CPC .... G06K 9/6267; G06N 20/00; G06T 11/003; G06T 2207/10072; G06T 2207/20081;
(Continued)

(56) References Cited

U.S. PATENT DOCUMENTS

2011/0122138 A1*  5/2011  Schmidt ............... G06K 9/6253
                                                 345/440
2016/0292878 A1* 10/2016  Hsieh ...................... G06T 7/174
(Continued)

OTHER PUBLICATIONS

Deng, Yubin, et al. "Aesthetic-driven image enhancement by adversarial learning." 201 Olin Library Cornell University Ithaca, NY. Jul. 2017. pp. 1-16.
(Continued)

*Primary Examiner* — Xin Jia
(74) *Attorney, Agent, or Firm* — Lempia Summerfield Katz LLC

(57) ABSTRACT

A method is provided for adapting an image impression of an image, in particular of an image acquired in the context of medical imaging. The method includes: providing an image or input data from which the image is acquired; specifying a respective ideal image impression class for the image and/or for at least one image segment of the image specified directly or by specifying at least one segment type, wherein a connection between the image data in the image and/or in the respective image segment and an assigned image impression class is specified by a classification algorithm; and modifying the image or the input data by a modification algorithm, in order to adapt the image impression class that has been assigned to the resulting modified image data pertaining to the image or pertaining to the respective image segment to match the respective ideal image impression class, wherein at least one modification parameter of the modification algorithm is or becomes specified as a function of the classification algorithm.

17 Claims, 6 Drawing Sheets

(51) Int. Cl.
*G16H 30/40* (2018.01)
*G06N 20/00* (2019.01)
*G06T 11/00* (2006.01)

(58) Field of Classification Search
CPC . G06T 2207/20084; G06T 2207/30004; G06T 2210/41; G06T 5/001; G16H 30/40
See application file for complete search history.

(56) References Cited

U.S. PATENT DOCUMENTS

2017/0236271 A1* 8/2017 Kim ............... G06K 9/6256
382/128
2019/0114766 A1* 4/2019 Song ............... G16H 15/00

OTHER PUBLICATIONS

European Search Report for European Patent Application No. 18199877.4-1210 dated Feb. 15, 2019.
Mansoor, Awais, et al. "Adversarial approach to diagnostic quality volumetric image enhancement." 2018 IEEE 15th International Symposium on Biomedical Imaging. Apr. 2018. pp. 353-356.
Xu, Zheng, et al. "Learning from Multi-domain Artistic Images for Arbitrary Style Transfer." 201 Olin Library Cornell University Ithaca, NY. May 2018. pp. 1-18.

* cited by examiner

METHOD FOR ADAPTING AN IMAGE IMPRESSION

The present patent document claims the benefit of European Patent Application No. 18199877.4, filed Oct. 11, 2018, which is hereby incorporated by reference.

TECHNICAL FIELD

The disclosure relates to a method for adapting an image impression of an image, in particular, of an image acquired in the context of medical imaging. In addition, the disclosure relates to a processing device, a computer program, and an electronically readable data carrier.

BACKGROUND

Images acquired in the context of medical imaging may be evaluated by medical professionals in the context of a diagnosis. In addition, relevant images are used to alert other people, for instance colleagues or patients, to specific features in the images. In this event, images directly acquired are not typically visualized, but a pre-processing of the acquired data ensues.

This is the case in particular when from acquired data, for example, from individual computed tomography X-ray images, first three-dimensional volume data and then, two-dimensional images, for instance sectional images or simulated X-ray images, are generated therefrom. It is known that the image impression of the acquired image or of individual features or segments in the image may depend on parameters selected in the context of image acquisition. For example, in the context of the reconstruction of a volume data set, various reconstruction kernels that may differ with respect to the achievable spatial resolution and the noise level of the result may be selected. According to the intended purpose, for example, depending on whether an image is intended to be used to visualize specific information for a patient or whether the image is intended to be examined for specific conspicuous features, and in particular depending on which conspicuous features are to be detected in which image region, a different parameterization of the pre-processing and therefore a different resulting image impression may be advantageous. In addition, it may be that different users desire different image impressions for the same purpose, as a result of which a pre-processing of the originally acquired data is required with different parameters in order to be able to provide ideal images for various users in each case.

Because it is not necessarily known to the users which processing parameters are ideal for them or for a given task, it may be necessary to carry out a plurality of processing procedures of acquired data until a desired result is achieved. Because a use of an iterative reconstruction of image data, for example, results in a relatively high processing effort to provide a new image, a change in the desired image impression may therefore lead to significant delays and therefore disrupt a user's workflow.

SUMMARY AND DESCRIPTION

The disclosure is therefore based on the object of improving the workflow in an evaluation of image data by a user.

The scope of the present disclosure is defined solely by the appended claims and is not affected to any degree by the statements within this summary. The present embodiments may obviate one or more of the drawbacks or limitations in the related art.

The object is achieved by a method that includes the following acts: providing an image or of input data from which the image is acquired; specifying a respective ideal image impression class for the image and/or for at least one image segment of the image that has been specified directly or by specifying at least one segment type of the image, wherein a relationship between the image data pertaining to the image and/or to the respective image segment and an allocated image impression class is specified by a classification algorithm; and modifying the image or the input data by a modification algorithm, in order to adapt the image impression class assigned to the modified image data pertaining to the image or to the respective image segment and resulting from the modification to match the respective ideal image impression class, wherein at least one modification parameter of the modification algorithm is or becomes specified as a function of the classification algorithm.

It is therefore proposed to modify an image impression of an image or of specific segments or of specific segment types of an image not by processing original data pertaining to the image once again with other parameters, but instead of this by modifying the image itself by a modification algorithm. Here, a modification algorithm that is or becomes parameterized by a classification algorithm is used. As will be explained later in greater detail, a relevant parameterization may ensue, by a machine learning method, for example. In principle, however, a manual parameterization would also be possible while considering a specified classification algorithm.

The proposed procedure makes it possible, as soon as a relevant modification algorithm is ready, to adapt the image impression of the entire image or of specific segments or segment types of the image as required. Here, such an adaptation may ensue manually according to a user's specific requirements or an adaptation may ensue automatically as a function of specific parameters, as will be explained later in even greater detail. Due to the option for rapidly adapting an image impression, it becomes possible as required for a user to rapidly switch between image impressions in order, for example, to locate an image impression for the image that supports them particularly well in their task without interrupting their workflow, for example. The procedure additionally makes it possible to also adjust different image impressions for different segments or different segment types of the image. For example, it may be achieved that features in some image segments are sharpened up, while in other image segments a reduction of noise ensues. This would be very complex with other methods because original data would have to be processed in a different way and the resulting image would have to be assembled from a plurality of these processing results in order to achieve locally different image impressions.

The classification algorithm is not necessarily used in the method itself. If the modification parameters of the modification algorithm are determined in a previous act and are therefore not as part of the method itself, it is sufficient if the classification algorithm is available in the previous act. The classification algorithm may, as explained later in even greater detail, be parameterized, in particular by a machine learning method.

The modification algorithm may include a plurality of modification parameters, which may be determined in the context of the method or in a previous act as a function of the classification algorithm. This may ensue by machine learning. Here, as will be explained later in greater detail, the classification algorithm and the modification algorithm may be trained together. For example, in the context of training, these algorithms may together form a Generative Adversarial Network (GAN), with the modification algorithm working as a generator and the classification algorithm as a discriminator.

The image impression class may be a sharpness of the image or of the image segment, for example, or a form of view, for example, whether connected areas are shown only as outlines, as a brightness and/or a contrast, whether specific features are shown at all or relate to similar things. The ideal image impression classes for individual image segments or segment types may be specified directly. Alternatively, an ideal image impression class may be specified for the entire image or for a viewing task that specifies respective ideal image impression classes for a plurality of image segments or segment types. For example, it may be specified that a specific organ is to be shown in sharp focus, while other image segments are to be shown with low noise.

A segment type may, for example, be a specific anatomical label, it being possible with the modification algorithm itself or with a preceding image segmentation to detect the image segments that are assigned to a corresponding label. Here, segment types may describe individual organs, bones, or suchlike. It is also possible for a segment type to describe an entire group of features. For example, the segment type may assign bones to all image segments in the image that show bones or similar features.

In order to modify an image impression class for a specific image segment, in the simplest scenario, the modification algorithm may be applied exclusively to data pertaining to this image segment. This may ensue through the image being previously segmented manually or automatically, for example, by a segmentation algorithm trained by machine-learning. However, the modification algorithm itself may detect all relevant image regions, (for example, image segments of a specific segment type), and modify them. It is not necessary here for the modification algorithm to explicitly output a segmentation or image data assigned to specific segments. It is sufficient, rather, if the result is achieved that the image impression class for the image segment that has been specified directly or via a segment type is configured to match the ideal image impression class specified for this image segment or for this segment type.

An adaptation of the image impression class of an image or image segment may lead to the image impression class of the image or image segment subsequently being identical to the ideal image impression class. It is also possible for the image impression classes to be arranged in a specific way. A one-dimensional arrangement may ensue here, (for example, an arrangement according to the degree of sharpness of the image or image segment), but a multi-dimensional arrangement is also possible, (for example, an arrangement according to the degree of sharpness and contrast). Adaptation may be understood here to mean that the image impression class of the image or segment is closer to the ideal image impression class after the application of the modification algorithm than it was for the original image or image segment.

The image data may be two-dimensional image data. In particular, two-dimensional image data that is generated from two-dimensional volume data may be involved, for example, sectional images or artificial projections.

The input data may be a plurality of two-dimensional images that are combined to provide the image. For example, the input data may be a masked image prepared in the context of an angiogram and an image taken with contrast agent and the image may be acquired by subtracting these images one from the other. To modify the image, the resulting image may be modified. It is also possible to modify the input data, (for example, the contrast agent image or the masked image), separately by the modification algorithm, in order to modify the image indirectly in this way.

The modification parameter may be or may become determined by machine learning. In the simplest scenario, the classification algorithm may be specified as fixed. For example, the classification algorithm may be a previously trained Convolutional Neural Network. With the aid of the classification algorithm, an unsupervised learning of the modification parameters may ensue, that is, it is not necessary to specify, for example, in the form of images that have already been modified, the results that are to be achieved. For training the modification algorithm, it may be sufficient to specify a training data set that includes exclusively the images to be modified and instructions as to how they are to be modified.

The modification parameters in the modification algorithm, that is, for example, weighting factors for individual neurons when a neural network is trained as a modification algorithm may first be initialized arbitrarily, for example, at random. As input data, a respective image and a respective desired modification, that is, an ideal image impression class for the entire image or for specific segments or segment types is specified to the modification algorithm, for example. With the aid of the known classification algorithm, after the modification of the respective image, it is possible to check whether this has been successful or how successful this has been. This may subsequently be used to modify the modification parameters of the modification algorithm. The modification algorithm may be a generative network or a deconvolution network. Such neural networks are particularly suitable for generating or modifying specific image data.

The training of the modification algorithm, that is, the determination of the modification parameters, may be a process act in the method. It is also possible, however, for this training to be arranged upstream as a separate process. To this extent, the disclosure also relates to a method for training a modification algorithm which is used to modify an image or segments of the image to modify an image impression.

For training the modification algorithm, pre-segmented images that are to be modified by the modification algorithm may be used. The segmentation may ensue manually or with a segmentation algorithm, in particular, one trained by a previous machine learning process. Here, segment types may be assigned to the individual segments or to groups of segments. In principle, it is possible to make segmentation information relating to the segmentation also available as input data to the modification algorithm. This may be advantageous, for example, if the modification algorithm is to be trained to modify pre-segmented images.

It may also be advantageous, however, not to evaluate the segmentation information in the context of the modification algorithm but to use it exclusively to acquire image impression classes for the individual specified segments of the modified image data by the classification algorithm and compare these with the ideal image impression class for the corresponding segment or for the corresponding segment type and adapt the modification parameters as a function of this comparison. In this case, the modification algorithm may additionally receive as input data pairs of segment types and ideal image impression classes specified for the segment types. The modification algorithm is therefore trained to detect independently which image regions have to be modified in which way in order to achieve an adaptation of the image impression class of image segments of a specific segment type to an ideal image impression class. In this way, it is possible to avoid artefacts, for example, which may result when different image segments of the image are modified in a different way in order to achieve different image impression classes for these segments.

At least one classification parameter in the classification algorithm and the modification parameter may be or may become determined together by a machine learning method. Here, in particular, a supervised training of the classification algorithm may first be carried out. For example, a training data set may include a plurality of images for this purpose, with respective image impression classes being assigned to the images or to the individual segments or segment types of the images, for example, by a previous manual classification. The classification algorithm may be a neural network, for example, such as a Convolutional Neural Network. Approaches to the supervised learning of classification algorithms are basically known and therefore are not to be explained in detail. For example, back propagation of error may be used to minimize a deviation between an image impression class that has been specified by the classification algorithm and the image impression class specified by the training data set.

A subsequent combined training of the classification algorithm and modification algorithm allows a further continual improvement of the classification algorithm and ultimately therefore of the modification algorithm, too. Here, the classification algorithm and the modification algorithm may be trained alternately, or a combined training may ensue.

In the context of machine learning, a learning algorithm may try either at the same time or alternately to select the modification parameter such that, when the classification algorithm is applied to a resulting image that is acquired when the modification algorithm is applied to an initial image, or to an image segment of the resulting image that has been specified directly or by specifying at least one segment type, a specified ideal image impression class is determined. Additionally, the learning algorithm may try to select the classification parameter such that when the classification algorithm is applied to the resulting image or to the at least one image segment of the resulting image and to the initial image or to an image segment of the initial image that is assigned to the image segment of the resulting image, the same image impression class is determined.

In other words, an attempt is made to at the same time to train the modification algorithm such that the image or the segment in a subsequent application of the classification algorithm has the specified ideal image impression class while the classification algorithm is trained to detect such a manipulation. A possible approach to this is to train a Generative Adversarial Network (GAN) in which the modification algorithm is used as a generative network and the classification algorithm as a discriminator. Through the learning approach that has been described, it is achieved in particular that, apart from the prior training of the classification algorithm, the training of the modification algorithm may ensue unsupervised, that is, that no ideal results have to be specified for the modification algorithm because, instead of a comparison with an ideal result, the learning ensues with the aid of the classification algorithm. Depending on the number of image impression classifications to be differentiated, it may also be advantageous to use a plurality of parallel or combined neural networks to determine the classification parameters and modification parameters.

In the context of training, respective ideal image impression classes may also be specified for a plurality of segments or segment types. In this case, the above explanation applies to each pair including image segment of the resulting image and assigned image segment of the initial image.

The image or the input data may be or become acquired from original data by a processing algorithm that is dependent on at least one processing parameter, with the image impression class of the image and/or of the respective image segment and/or segment type being dependent on the processing parameter. The processing of the original data may be part of the method but may also be carried out in a previous act, such that the image or the input data are already provided for the method. Here, the classification algorithm may be specified such that, or the at least one classification parameter of the classification algorithm may be acquired such that image impression classes determined by the classification algorithm are dependent on the respective processing parameters used. This may ensue by machine learning, for example. For example, supervised learning may be implemented, the image or the input data may be generated from a plurality of specified original data sets each with different processing parameters. Here, firmly specified image impression classes may be assigned to sets of processing parameters, for example, based on prior knowledge about the action of these processing parameters. Therefore, the training data set for each image or for each initial data set may include an image impression classification assigned to the processing parameters. If the classification algorithm is implemented as a neural network, for example, then the learning may subsequently ensue through a comparison of the image impression classification that has been acquired and the image impression classification stored in the training data set and classification parameters of the classification algorithm may be adapted, for example, by a back propagation of error.

The processing parameter may have an influence, for example, on the image sharpness or image noise in the image or in specific segments of the image. This may be the case, for example, if the processing algorithm adapts a folded kernel as a function of the processing parameter or suchlike. The image impression classes determined by the classification algorithm may indicate in this case, for example, how sharply or softly drawn an image or a specific segment of the image is. In this case, the modification algorithm may subsequently serve to later smooth out or sharpen the image accordingly.

The processing algorithm may include a reconstruction algorithm for the reconstruction of three-dimensional volume data from two-dimensional original data, in particular from X-ray images, with the reconstruction algorithm being a function of the processing parameter or of at least one of the processing parameters and/or with the image or the input data being two-dimensional image data generated by a mapping algorithm from the volume data, with the mapping algorithm being a function of the and/or of at least one of the processing parameters. For example, the three-dimensional volume data may be generated in the context of computed tomography from two-dimensional X-ray images, for example, by a filtered back projection, an iterative reconstruction or suchlike. The image data or input data may be slice images or synthetic X-ray images generated from the volume data.

The reconstruction parameter may relate to a selection of a reconstruction kernel or the parameterization thereof. For example, a reconstruction kernel may be selected such that the volume data indicates Hounsfield units or a reconstruction kernel that highlights edges may be selected.

In the method, different ideal image impression classes may be specified for different image segments and/or different segment types. For example, there may be a desire in a specific relevant region, for example, in the region of a specific organ, that a particularly sharp representation ensues or that edges are highlighted, whereas in the surrounding background region on the other hand, noise suppression is desired, even when this may lead in some cases to a reduction in the spatial resolution. There may also be a desire not to show specific segment types that are of little relevance to a current visualization, or for example, to show them with lower brightness or low contrast, so that relevant features may be detected more quickly and more easily. Different views and therefore corresponding sets of ideal image impression classes may be selected automatically or manually as required for the different image segments or segment types. For example, it is possible by the corresponding selection of the ideal image impression classes to achieve that, based on the same image, or the same input data, either bones or the vascular system may be highlighted to a greater extent as required.

The ideal image impression class and/or the at least one image segment and/or the at least one segment type for which the ideal image impression class is specified may be specified as a function of a user's operating input and/or of user information identifying the user and/or of the image and/or of the input data and/or of the original data and/or of additional information relating to the imaging of the image and/or to a patient shown in the image. This may serve, for example, as soon as an image is opened by a user, to modify the image automatically such that an image impression suitable for a specific user or for a specific task is created. It is also possible, however, for the aforementioned parameters only to be used to support a user in the selection of an appropriate modification. For example, it is possible as a function of these parameters for only specific modifications to be suggested or, for example, adjusted to the sequence of proposed modifications. These approaches may also be combined. For example, an automatic modification of the image may first ensue, and the user may switch to other modifications as required, with an appropriate selection being offered to them for this purpose.

A specification of the parameters may advantageously ensue as a function of the user information in order to adapt a displayed modified image to match a user's preferences. This may be learned continuously, for example. For example, it may be necessary initially for a user not yet known to the system to have to select manually how an image is to be modified, that is, in particular which segments or segment types are to include which ideal image impression classes. Following one or a plurality of these inputs, the system may, by a method of machine learning or by a statistical evaluation of the inputs, taking into account in particular the respective use situation in which a relevant input has been made, learn the user's preferences and then, for example, already automatically select a modification or limit the proposed modifications according to these preferences. It is also possible in this case, following the learning of the user preferences, for the learning to be further continued, that is, for example, to set up a feedback loop in order to detect when the user in specific situations switches from the presumed optimum modification to a different modification, in order to detect changes in user preferences, for example.

The user information may be acquired by a user identifying themselves on the system, for example, by inputting a user identification, a keycard, or suchlike. It is also possible, however, to carry out an automated user identification. To this end it is possible for input patterns (e.g., a chronological sequence of keyboard inputs, mouse movements, the selection of specific program options, and suchlike), to be evaluated. It is therefore possible, for example, for a machine learning algorithm to be applied in order to identify users by their transactions on the system.

It may be advantageous for the ideal image impression class and/or the image segment and/or the segment type to be dependent on the image, on the input data and/or on the original data if, for example, an automatic detection of features in this data ensues. For example, it may be detected that features are present in a specific image segment that point to a lesion, a tumor or other anomaly. By selecting an ideal image impression class for this image segment or by other corresponding manipulations of the image, it is possible to achieve that corresponding features that in some circumstances are highly relevant are clear and simple for a user to detect.

As imaging parameters, it is possible to consider, for example, exposure times used, radiation intensities, or tube currents, a chronological sequence in the acquisition of the X-ray images, information subsequent to a sub-sampling, or suchlike. Imaging parameters may have a considerable influence on the representation of the features in the image, which means that it may be useful to adapt the way that an image is to be modified as a function of imaging parameters, that is, which ideal image impression class is selected for the image or for specific image segments or segment types of the image.

Information relating to the patient may be information from a patient file, for example. From this information it may emerge, for example, for what purpose the image was taken, or which task of representation or diagnosis is to be solved by the image. For the selection of a useful image impression, it may therefore be highly relevant whether a vascular system or bones that are shown in the image is/are more relevant for a current task of diagnosis.

The aforementioned list of parameters on which the selection of the ideal image impression class or of the modified image segments or segment types depends is not exhaustive. For example, previous operational inputs by the user, in particular, when viewing the same image, may be taken into account in addition in order to draw further conclusions relating to the user's wishes or it may be taken into account whether a visualization will ensue in a consulting room, for example, that is, in specific circumstances for a patient, on an instrument of measurement or on an office computer.

The specification of the ideal image impression class and/or of the at least one image segment and/or segment type for which the ideal image impression class is specified, and/or a specification of ideal image impressions selectable by the or a user or recommended to the user and/or image segments and/or segment types for which the image impressions are selectable or recommended or specified may ensue by a specifying algorithm that is or becomes parameterized by machine learning. The training may ensue by having parameters that are potentially relevant to a selection, for example, the parameters discussed in the aforementioned, being used for a specific use situation and a selection that has ensued in this use situation of the ideal image impression class or classes or of the segments to be modified or segment types being used by the user as training data. The specifying algorithm may be trained by supervised learning, wherein the manual selection specifies the ideal result of the specifying algorithm and the relevant parameters that have been determined specify the input values. Following a learning phase of the specification algorithm, a further monitoring by the user may ensue, in order, for example, to detect changes in the user habits.

The modification algorithm may be configured to automatically specify image segments and/or segment types and ideal image impression classes assigned in each case, as a function of a viewing task specified for the image. This may be useful when a manual selection of the image modification by a user is to ensue and different ideal image impression classes for different image segments or segment types are to be used at least for parts of the possible viewing tasks. In this case, it is advantageous to define a kind of macro which allows a user to carry out complex modifications to the image by selecting a specific viewing task.

In the context of a specific viewing task, but also independently thereof, it may be achieved by the specification of corresponding ideal image impression classes for the corresponding segments or segment types, for example, that specific features or segments that include these features are shown with low brightness or low contrast or are not shown or are only shown in diagram form. Non-representation of specific features may ensue by parts of the segments being replaced by a monochrome surface or a specific pattern. This may be advantageous when a specific state of affairs is to be visualized for a patient and features not relevant thereto are to be masked.

A schematic representation may ensue by only outlines of features detected in specific image segments being shown. This may be achieved by a gradient being created in these segments and a limit value comparison subsequently ensuing. Optionally, morphological operations may also be used in order to form enclosed outlines. Of course, abstractions that are even more extensive are also possible, for example, representing blood vessels exclusively by their center line or suchlike. If the image is acquired from input data that includes a plurality of images, for a digital subtraction angiogram, for example, it is also possible to show specific segments or segment types transparently. For example, depending on the viewing task or ideal image impression class selected, the background of an angiography image, that is, for example, bones and/or other organs, may be completely masked or shown with low contrast or low brightness to orient the user.

A possible example of a viewing task is removing bones from the image. Here, the bones may be pre-segmented, or they may be segmented by the modification algorithm itself. In this case, the viewing task may specify "remove bones", such that for the segment type bones, the content of the corresponding segments is not shown, is shown with lower brightness or lower contrast or is only shown schematically.

The image or the modified image data may be shown for the or a user, with at least one image region which includes a feature, the representation of which depends on the image impression classification of the image or at least of one segment of the image or depends on the viewing task, being marked. Specific features shown in the image may be detected only with difficulty in the image itself or in specific modified versions of the image. This may be desirable in some circumstances because it may improve the detection of other features. At the same time, the corresponding features may still be relevant for a current diagnostic task or suchlike. It may therefore be advantageous to highlight in particular image regions in which, in a current view, features that are difficult to detect or cannot be detected are located so as to indicate to a user that, by selecting other ideal image impression classes or another viewing task, this feature may be shown or shown more clearly.

In particular, provision may be made for the user to select marked image regions by a user input. For example, the image may be shown on a touchscreen and corresponding image regions may be touched by a user; they may be selectable with a mouse or suchlike. When selecting the highlighted image region, a different viewing task or a different ideal image impression class for the entire image or for at least one segment may be specified automatically or after consultation with a user in order to achieve a modified, in particular clearer, view of the feature by further modification of the image.

The image may be acquired by a superimposed view, in particular by subtraction, from source images described by the input data, with the modification algorithm processing the source images as input data. In particular, the image may represent a digital subtraction angiogram in which a masked image taken without contrast agent is subtracted from a contrast agent image taken with contrast agent in order to achieve clearer highlighting of the patient's vascular system. Here, in particular, CT angiography may be used in which a CT image may ensue with and without contrast agent, such that the contrast agent image and the marked image may be sectional images of a respective corresponding volume data set. In this case, it would indeed be possible in principle to apply the modification algorithm to the image resulting from the superimposition. The processing of the source images as input data makes it possible, however, to modify the source images separately from one another or to adapt the type of superimposition. It may therefore be desirable for a specific viewing task or a specific image impression, for example, that the organs that may be completely masked in the digital subtraction angiography image to be superimposed schematically or with full contrast. It may also be possible to subsequently superimpose the subtraction image that exclusively shows the vascular system with the masked image once again, wherein a different modification of the masked image and of the subtraction image ensues, that is, for example, the subtraction image is sharpened up, while the masked image is blurred or suchlike. A needs-based, flexibly adapted view may therefore be provided to a user.

An adaptation of a superimposed view where the source images are used as input data for the modification algorithm may also be used to present information from various parallel slices of a volume data set together in one image. As a function of the viewing task or of the ideal image impression class for the entire image or the individual image segment or the individual segment type, the modification algorithm may influence the superimposition, for example, such that in specific segments or segment types information is exclusively displayed about one of the slices or such that a superimposition ensues such that information from one of the slices is lying as a kind of transparent slice over the information for the other slice.

As already explained, the determination of the at least one classification parameter in the classification algorithm and/or the determination of the at least one modification parameter in the modification algorithm may ensue independently of the method as an act arranged upstream. The classification parameter and/or the modification parameter may be determined here by a respective method of machine learning or in particular together by a method of machine learning.

The disclosure also relates to a method for the determination of a classification parameter in a classification algorithm that serves to assign image data pertaining to an image and/or pertaining to a respective image segment to an image impression class, by a method of machine learning. This has already been explained in detail in the aforementioned.

The disclosure also relates in addition to a method for determining at least one modification parameter in a modification algorithm that serves to modify an image or input data from which the image is acquired, such that an image impression class, which is assigned by a classification algorithm to the resulting modified image data for the image or for a respective image segment of the image, is aligned with a specified ideal image impression class, the modification parameter being determined by a method of machine learning. In particular, the modification parameter and a classification parameter that parameterizes the classification algorithm may be determined together by a method of machine learning. The determination of the modification parameter or the combined determination of modification parameter and classification parameter have already been explained in detail in the aforementioned.

The disclosure also relates to an electronically readable data carrier, on which classification parameters and/or modification parameters and/or an implementation of a classification algorithm and/or of a modification parameter parameterized by the modification algorithm determined or determinable by the method explained in the aforementioned are stored.

Alongside the method, the disclosure also relates to a processing device for the processing of images, which device is configured to carry out the method. The processing device may be incorporated in particular in an X-ray device, for example, in a computed tomography unit, or be part in particular of an X-ray device for the acquisition of X-ray images, in particular a computed tomography unit. It is also possible, however, for the processing device to be a workplace computer or server that is programmed accordingly. Such a server may be an image acquisition device used locally in the same building, in particular an X-ray device, yet arranged apart therefrom. The processing device may also be embodied as a cloud-based system, which may be implemented by a plurality of servers, in particular arranged in different locations. The processing device may include a memory for storing data accrued in the context of the method. The storage device or a further storage device may in addition store a program that implements the method. The processing device may also include a processor that may carry out the acts in the method.

The disclosure additionally relates to a computer program that may be loaded directly in a memory of a processing device, with programming code or mechanisms to carry out the acts in the method when the program is run in the processing device.

The disclosure also relates to an electronically readable data carrier with electronically readable control information stored thereon, which information includes at least one computer program, and which is embodied such that it carries out the method when the data carrier is used in a processing device.

BRIEF DESCRIPTION OF THE DRAWINGS

Further advantages and details of the disclosure will emerge from the following exemplary embodiments and from the relevant drawings. In the drawings, shown schematically.

DETAILED DESCRIPTION

Figure 1:
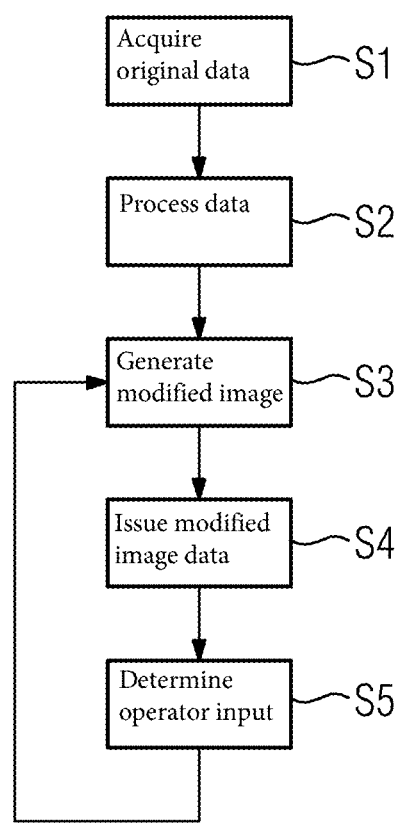
FIGS. 1 and 2 depict the sequence for an exemplary embodiment of the method.

FIG. 1 depicts a flow diagram of a method for adapting an image impression of an image, wherein in particular an image impression of an image that is acquired in the context of medical imaging may be adapted. The data and processing modules used in the context of the method are shown schematically in FIG. 2.

In act S1, original data 1 that may be individual X-ray images that have been taken in the context of computed tomography of a patient, for example, are first acquired. This data is processed in act S2 by a processing algorithm 15, which is dependent on processing parameters 3, 6, in order to provide the image 7. Here, an image impression of the image 7 or of individual image segments 16, 17 of the image 7 may be dependent on the processing parameters 3, 6. Such an image impression may be quantified by applying a specified classification algorithm 13 to the image 7 or to individual image segments 16, 17 of the image 7 in order to determine a respective image impression class 14. As will be explained later in even greater detail, such a classification algorithm may be defined or parameterized by a machine learning method, for example.

In the exemplary embodiment shown, the processing algorithm 15 includes a reconstruction algorithm 2, which reconstructs three-dimensional volume data 4 from the two-dimensional original data 1. This algorithm is parameterized by the processing parameters 3 that may indicate which reconstruction kernel is to be used in the context of the reconstruction. For example, a reconstruction may ensue such that the volume data 4 indicates Hounsfield units for individual points in the volume. It is also possible, however, for edges to be highlighted in the volume data. In addition, it is optionally possible, as a function of the reconstruction that is used in practice, for example, for a higher spatial resolution or a better signal-to-noise-ratio to be achieved. The processing parameters 3, on which the reconstruction algorithm 2 depends, may therefore directly influence the image impression and consequently the image impression class for the entire image 7 or the individual image segments 16, 17.

In the context of the processing algorithm 15, the volume data 4 is subsequently represented by a mapping algorithm 5 that is parameterized by further processing parameters 6 in order to generate the image 7. The mapping algorithm may generate slice images or synthetic X-ray images from the volume data 4. The processing parameters 6 may describe which slice thickness ensues perpendicular to an image plane in the generation of slice images or to what extent a blurring or sharpening ensues in the context of the figure is considered. These parameters also influence the image impression and hence the image impression class of the image 7 or image segments 16, 17.

Here, different image impressions may be advantageous for various diagnostic purposes. Moreover, different users prefer different image impressions. In order to avoid the complete processing algorithm 15 having to be carried out again to change an image impression each time, which may be very processing-intensive in some cases, for example, when an iterative reconstruction algorithm is used as a reconstruction algorithm 2, it is possible in act S3 to use a modification algorithm 8 in order to generate modified image data 12. Here, the modification ensues such that the image impression class 14, which is assigned via the classification algorithm 13 to the modified image data 12 of the entire image 7 or to the modified image data 18, 19 of the respective image segments 16, 17, corresponds to a specified ideal image impression class 9.

Figure 5:
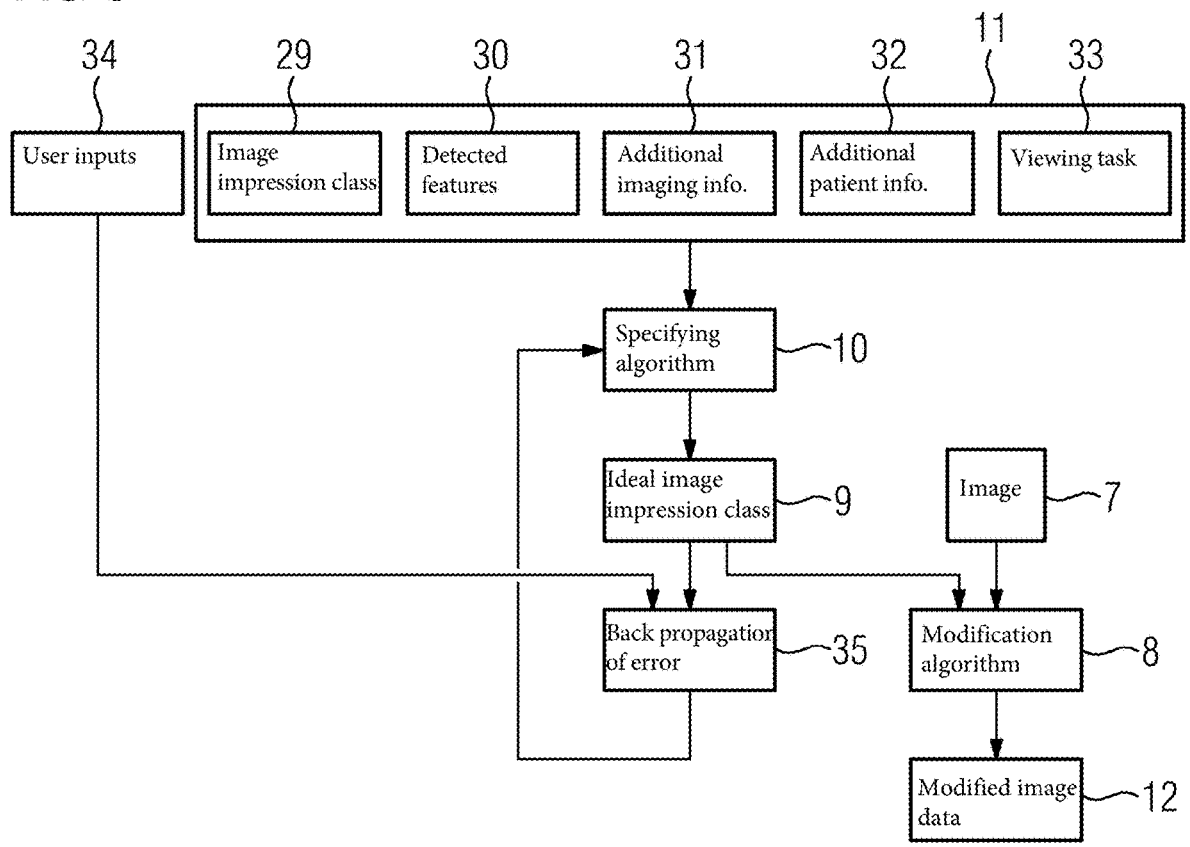
FIG. 5 depicts a further exemplary embodiment of the method.

The ideal image impression class 9 is determined in this case from specified data 11 by a specifying algorithm 10, which as will be explained again later in greater detail, may be parameterized in particular by machine learning. The specified data 11 may relate to the user so as to align the image impression with user preferences. In addition, this data may relate to the practical situation where it is used, that is, for example, a task of viewing or diagnosis. Various possible specified data is further discussed again later with reference to FIG. 5.

The modification of the image 7 may already ensue in act S4 before the issue of the image 7 to a user. For example, it may already be detected, by available specified data or of a user identification, that a specific image impression will probably be advantageous. Following the issue of the modified image data 12 in act S4, an operator input may be determined in act S5, as a function of which a fresh modification of the image 7 in act S3 is carried out, which is adjusted according to the operator input. The procedure described may be repeated as often as necessary in order to provide a user with optimum information. The operator input determined in act S5 may be considered in the next application of the modification algorithm, in particular as part of the specified data 11.

The procedure described may be modified such that an image 7 is not modified directly, but rather input data from which the image 7 is acquired or the modification of the image may ensue such that an acquisition of the image from input data is modified. The input data may be in particular a plurality of two-dimensional images, which are superimposed or subtracted in order to acquire the image. For example, it may be the case of a masked image and a contrast agent image that are subtracted one from the other in the context of digital subtraction angiography. Here, the individual images for the input data may be generated as explained for FIG. 2 such that first the respective two-dimensional original data 1 from which input images are generated in each case, is reconstructed into respective volume data 4. This is useful, for example, in order to provide a masked image and a contrast agent image. However, the input images may also be different images generated from the same volume data 4, for example, different slice images, which may be shown superimposed. By using a plurality of two-dimensional input images for the determination of the image and the modification of the images or of the superimposition thereof, a resulting image impression may be further adapted, for example, by it being specified as to which of the segments 16, 17 of the image data shows which input image, or how the image data in the input images is weighted in the event of superimposition.

Figure 3:
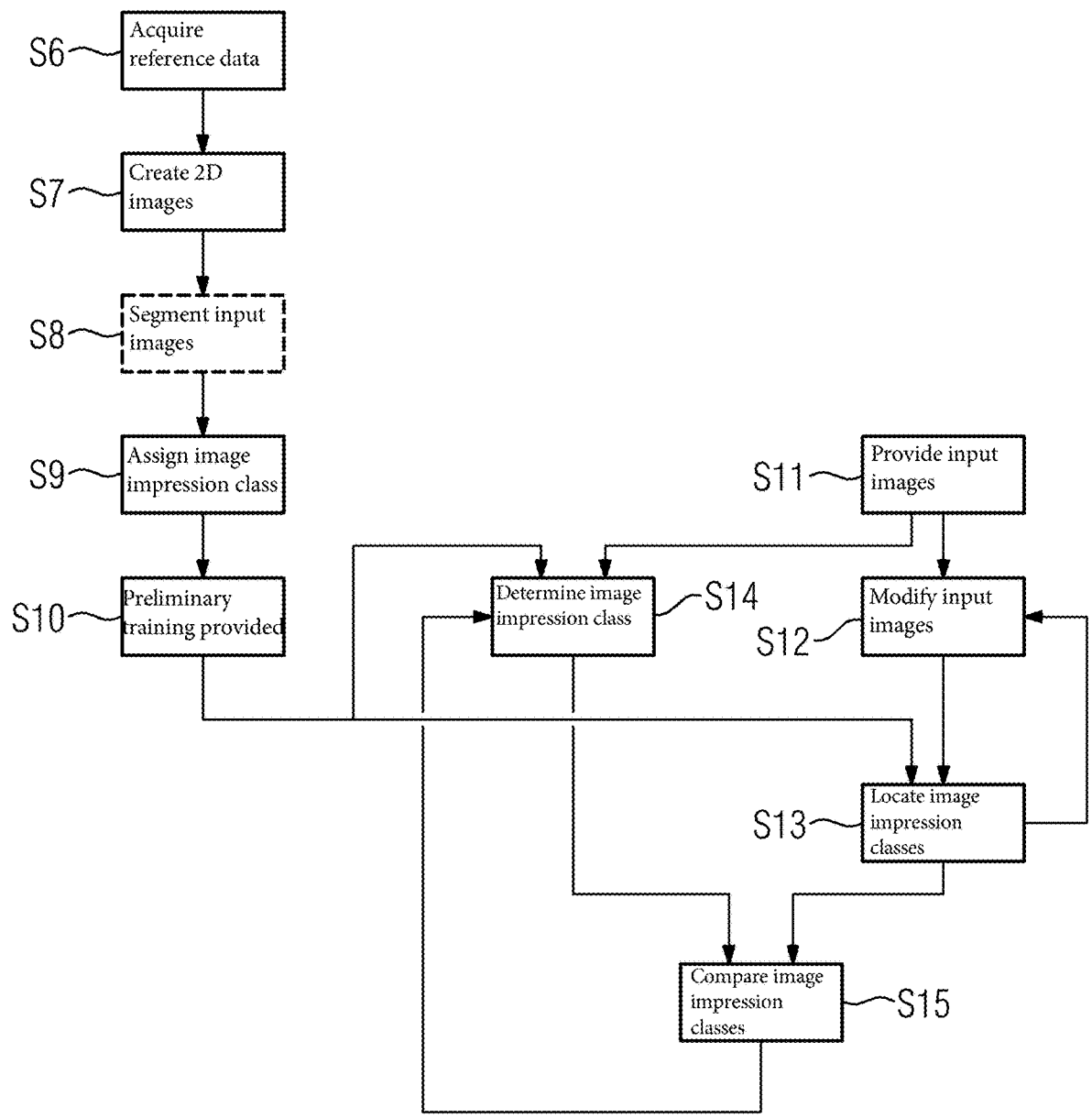
FIGS. 3 and 4 depict examples of the training of a modification algorithm that may be used in the method depicted in FIGS. 1 and 2.
Figure 4:
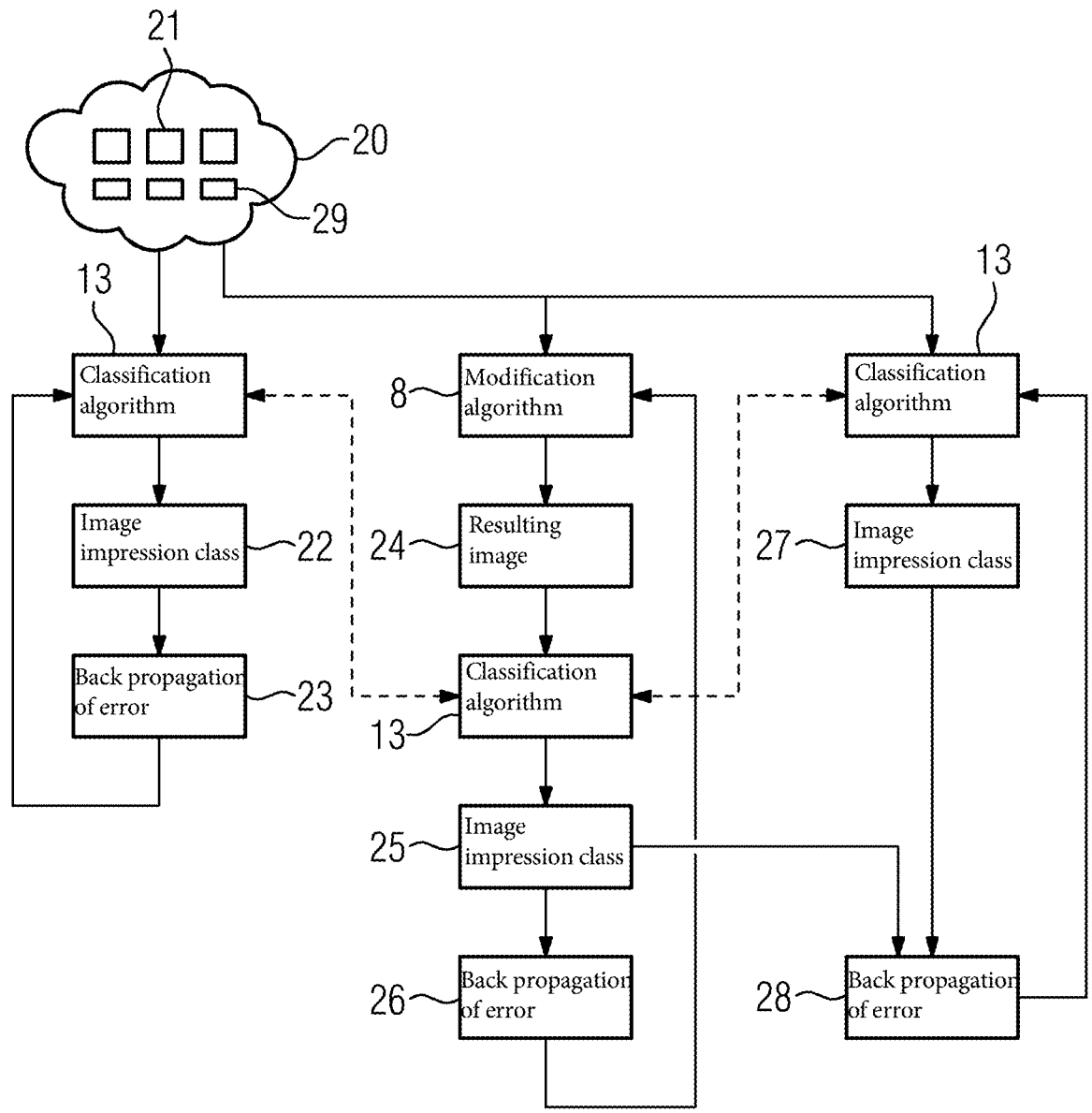

FIGS. 3 and 4 depict a method for determining classification parameters in the classification algorithm 13 and for determining modification parameters in the modification algorithm 8, which method may be carried out as part of the method described in the aforementioned but also in preparation for the method described, independently thereof.

Figure 2:
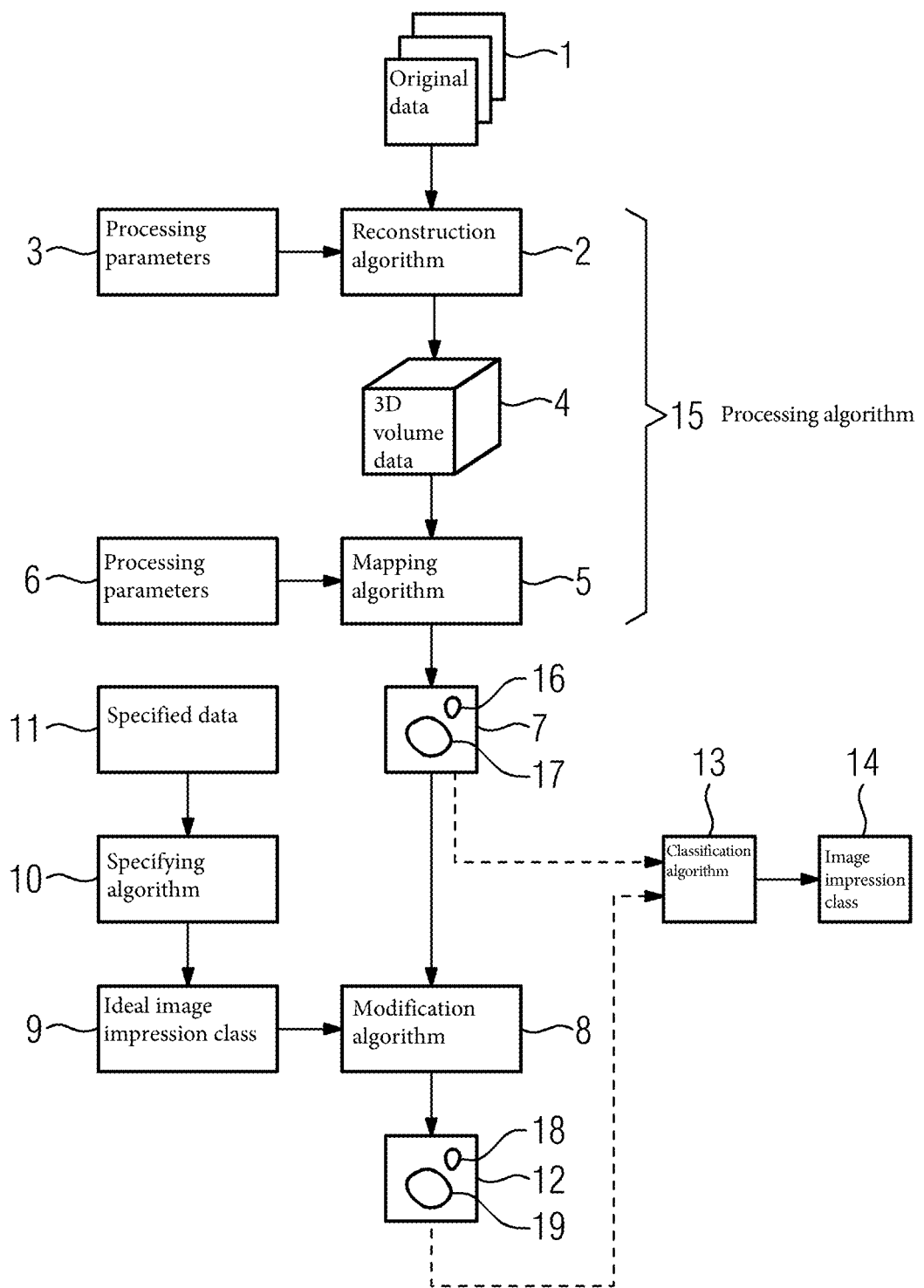

Here, FIG. 3 depicts a flow diagram of the method and FIG. 4 the data structures and algorithms used therein. Acts S6 to S9 serve here for the preparation of a training data set 20, which is used for training the classification algorithm 13 and which may also provide images for training the modification algorithm 18. For this purpose, reference data is first acquired in act S6. For example, a plurality of computed tomography images may be acquired for various patients. The processing algorithm 15 descried with reference to FIG. 2 is used in act S7 for the individual reference data sets in order to first generate volume data sets and create two-dimensional images therefrom. Here, the processing parameters 3, 6 are varied in order to generate a plurality of input images 21 for each of the reference data sets acquired in act S6, which images differ from one another with regard to the different processing parameters 3, 6 used in the context of the processing of the image impression in the entire image or with regard to the image impression in individual image segments.

In act S8, there ensues a segmentation of the input images 21. If the classification algorithm is to be trained exclusively for classifying the image impression for the entire image, or if the modification algorithm is to be trained exclusively to modify the image impression of the entire image, then act S8 may be dispensed with. The segmentation may ensue manually by one or a plurality of experts. In certain examples, a segmentation may ensue in act S8 by an algorithm for the automatic segmentation of the input images 21. Such an algorithm may be trained in advance, by machine learning, for example, by a manual pre-segmentation ensuing for a sufficiently large number of images and the algorithm being trained in the context of supervised learning such that the segmentation carried out approaches the specified segmentation as closely as possible.

In act S9, a respective image impression class is assigned to each resulting image or, if this has occurred beforehand, to the individual segments of the resulting image. It is also possible for this assignment to ensue not for individual segments but for segment types, that is, for example, for all the segments that show the bones or part of a vascular system. Assignment may ensue exclusively by the input images themselves either manually or by one or a plurality of experts. However, because it may be assumed that, at least for all segments of a specific segment type, a strong correlation exists between the image impression in the input images or image segments and the processing parameters 3, 6 used for the images, it is also possible to assign a specific image impression class 29 to the various combinations of processing parameters or to specific ranges of values of processing parameters or for a specific segment type. In this way, it may be avoided that all input images 21 have to be classified manually because it is sufficient to define an appropriate assignment between processing parameters 3, 6 and the image impression class 29.

As the result of act S9, a training data set 20 is therefore provided which includes a plurality of input images 21 and image impression classes 29 assigned to the respective input images 21 or to the individual image segments of the input images 21. With the aid of this training data set 20, a preliminary training of the classification algorithm 13 first ensues in act S10. The classification algorithm 13 is used at a plurality of points in the method described. In order to achieve an image that is as clear as possible, the classification algorithm 13 is therefore shown several times in FIG. 4. However, as indicated by the dotted double arrows and the identical reference signs, the same classification algorithm 13 is involved here.

The classification algorithm 13 may be trained by supervised learning. The training serves to determine a plurality of classification parameters. If the classification algorithm 13 is an artificial neural network, for example, a Convolutional Neural Network, then the classification parameters may be the input weights of individual artificial neurons. The initial values of the classification parameters may be specified arbitrarily, for example, be selected at random. In the context of the training, the classification algorithm 13 that has been parameterized accordingly is applied in each case to at least one of the input images 21 to determine an image impression class 22 for the entire image and/or for the segments previously determined in act S8. Through a back propagation of error 23, the image impression class 22 that has been determined is compared with the impression class 29 specified in act S9 and as a function of this comparison, the classification parameters of the classification algorithm 13 are adapted. Relevant methods for the supervised learning of classification algorithms are known in principle and are therefore not to be discussed in detail.

After sufficient training of the classification algorithm 13, for example, after a firmly set number of training iterations or after the fulfillment of a convergence criterion for the classification parameters, the supervised learning of the classification algorithm 13 is initially complete. The following acts serve for carrying out a combined unsupervised learning of the classification algorithm 13 and of the modification algorithm 8. Here, the input images 21 in the training data set 20 may indeed continue to be used, but other input images may also be used at random, because the assigned specified image impression classes 29 are now no longer required. The learning structure used hereinafter has the structure of a Generative Adversarial Network, with the modification algorithm 8 serving as a generator and the classification algorithm 13 as a discriminator.

In act S11, input images, which may be the input images 21 of the training data set 20 or even other input images, are first provided. In addition, an ideal image impression class is specified in each case for the input images or specific segments or segment types, in order to train the modification algorithm 8 to achieve this ideal image impression class for the image or image segment or all segments of a segment type.

In act S12, the input image is modified by the modification algorithm 8. This modification depends on the modification parameters of the modification algorithm. The modification algorithm may be a neural network, for example, a "deconvolutional" or unfolding neural network. In this case, the modification parameters may be the input weights of individual artificial neurons. The modification parameters may first be selected arbitrarily, for example, at random. A resulting image 24 is issued as a processing result.

In act S13, the classification algorithm is used to locate the image impression classes of the resulting image 24 or of the individual segments of the resulting image 24. Here, the classification algorithm 13 is first parameterized by the classification parameters that have been determined in the training described in the aforementioned. These may be modified, however, as will be explained again later, in the course of further training. If a classification for individual image segments is to be determined, the resulting image 24 may be segmented beforehand. It is particularly advantageous, however, if the input images provided in act S11 are segmented and a corresponding segmentation is transferred to the resulting images 24 unmodified. Various options for segmentation have already been explained with reference to act S8.

The image impression classes 25 determined for the modified image data 24 or image segments thereof are compared by the back propagation of error 26 with the ideal image impression classes specified in act S11 for the corresponding image or corresponding image segment and the modification parameters of the modification algorithm 8 are adapted depending on the result of the comparison.

In order to achieve a more robust training of the modification algorithm 8, it is advantageous to further train the classification algorithm 13 such that it tries to continue to detect the same image impression class despite the modification by the modification algorithm 8. As a result, thereof, it is possible in particular to avoid the modification algorithm being trained to modify the image in a way that barely changes the actual image impression but leads to a misclassification of the image impression. In order to achieve this parallel training, in act S14 the classification algorithm 13 is applied to the same input images that are also supplied to the modification algorithm 8 in order to determine a respective image impression class 27 for the unmodified input images or the image segments thereof. The individual image impression classes 27 for the unmodified input images are compared in act S15 by the further back propagation of error 28 with the corresponding image impression classes 25 for the resulting images 24. As a function thereof, the classification parameters of the classification algorithm 13 are adapted, wherein the optimization is intended to ensue such that, where possible, the image impression classes 27 for the input images or segments thereof correspond considerably with the image impression classes 25 for the resulting images 24 or segments thereof.

The acts S12 to S15 are repeated, for example, for a specified number of iterations or until a convergence criterion for the modification parameters and/or the classification parameters is fulfilled. Because an unsupervised learning process is involved, the number of iterations is not limited by the number of training data sets available. Therefore, a qualitatively high-value training of the modification algorithm may be achieved, the training quality being limited in any case by the quality of previous training of the classification algorithm 13.

As already explained with reference to FIG. 2, the specification of the ideal image impression class 9 for the image 7 or the ideal image impression classes 9 for the segments 16, 17 of the image 7 may ensue by a specifying algorithm 10, which is trained by a machine learning method. This is explained in greater detail hereinafter on an exemplary embodiment with reference to FIG. 5. Here, the aim of training is for specified data 11 to be evaluated automatically by the trained processing algorithm 10 in order to determine for a user and a current use situation particularly well suited ideal image impression classes 9 for the image segments 16, 17 of the image 7, such that image data 12 that has been modified accordingly may be provided by the modification algorithm 8. This procedure has already been explained in the aforementioned with reference to FIG. 1 and FIG. 2.

Used as specified data 11 in the exemplary embodiment shown are user information 29 that identifies a user, features 30 detected in the image, additional information 31 relating to the imaging, additional information 32 relating to the patient, and a viewing task 33 specified by the user, which task is intended to indicate, for example, for which type of diagnosis image data is to be provided.

The specifying algorithm 10 may be a neural network, for example, wherein in the context of training, for example, parameters are determined which describe the input weights of the artificial neurons in the network. A supervised learning may be used, that is, in addition to the specified data 11, user inputs 34 are determined at least in a training phase, which inputs specify directly for which image segments 16, 17 or segment types which ideal image impression classes 9 are to be present in the modified image data 12. The ideal image impression classes determined by the specifying algorithm 10 may then be compared in the context of a back propagation of error 35 with the ideal image impression classes specified by the user input 34. The parameterization of the specifying algorithm 10 may be adapted accordingly in order to minimize deviations between the information sets.

After an initial learning phase, the additional input 34 is dispensed with. It is possible, however, for the user to continue to activate the input 34, for example, when the automatically specified ideal image impression classes 9 are not suitable in his opinion to adapt the image impression as required. Then when a user input 34 ensues, this may be used to further train the specifying algorithm 10.

Figure 6:
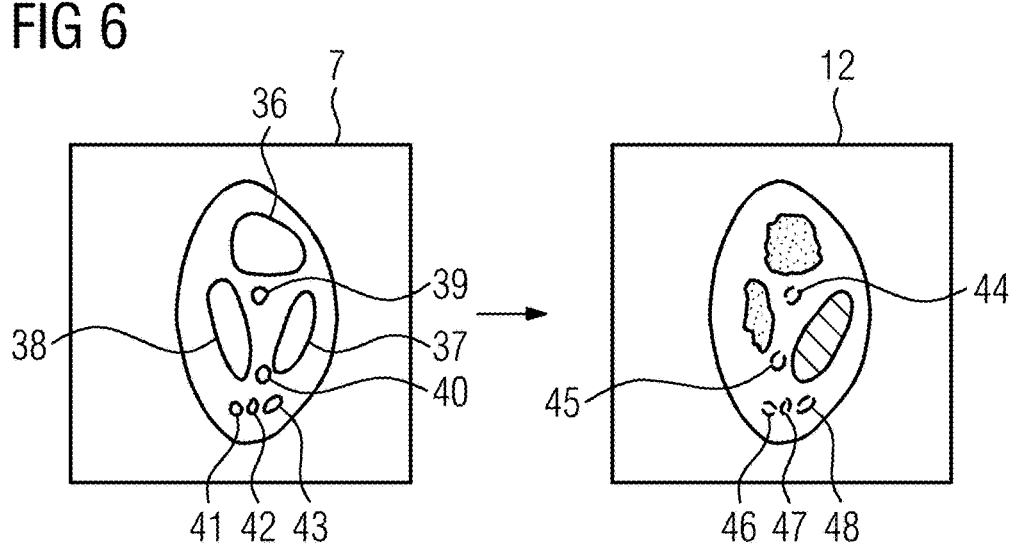
FIG. 6 depicts the display of modified image data in an exemplary embodiment of the method.

FIG. 6 depicts schematically an example of a modification of an image 7 by the modification algorithm 8. Here, the original image 7 shows a plurality of features 36 to 43, which are to be detected approximately with the same clarity. If a user would like, for example, to highlight the feature 37 for a specific diagnostic purpose or for a visualization for a patient, ideal image impression classes may be specified for the segments that include the individual features 36 to 43, such that the feature 37 is highlighted, that is, for example, with particularly strong contrast and particularly sharply. The features 36, 38 may be blurred, for example, such that they may indeed continue to provide further information to an observer about the position of the feature 37 yet cannot divert from this feature 37. The relatively small features 39 to 43 cannot or may barely be detected in the modified image data 12. In order to indicate to a user, however, that these features are present and may be made visible or be highlighted by selecting a different image modification, the image regions 44 to 48 in which the features 39 to 43 cannot or may barely be detected in the modified image data 12 may be highlighted, for example, by surrounding the relevant regions with a colored dotted line.

Figure 7:
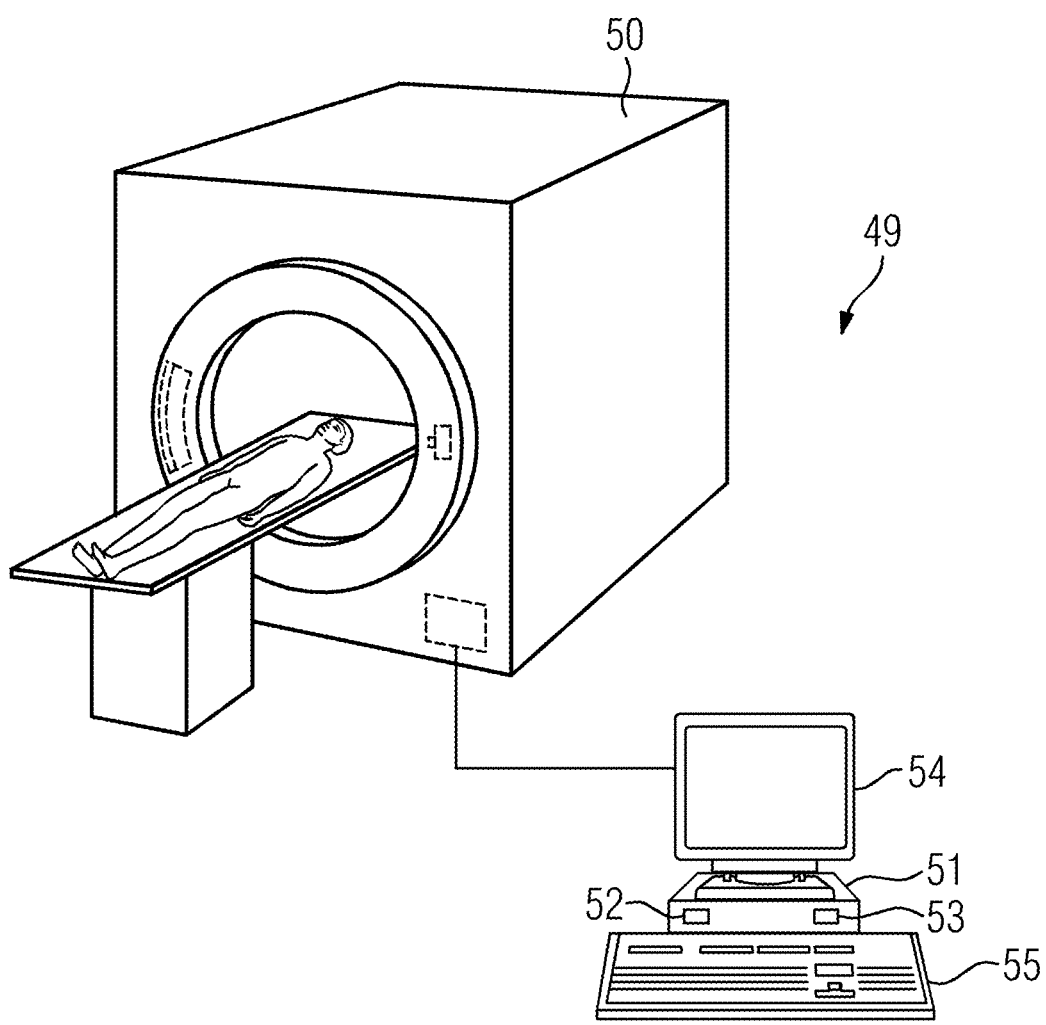
FIG. 7 depicts an exemplary embodiment of an X-ray system that includes a processing device.

FIG. 7 depicts an X-ray system 49, which includes an X-ray device 50, that is, a computed tomography unit, and a processing device 51. The processing device is configured to process the original data provided by the X-ray device 50 in order to display images, in particular sectional images, for a user on a display device 54. When required, the processing device 51 may modify the images by a modification algorithm according to the method set out in the aforementioned in order to specify ideal image impression classes for the images or for individual image segments or segment types. A modification may already ensue the first time the image is displayed. In order to achieve this, a similar approach may be used to that described with reference to FIG. 5, with training of the specifying algorithm 10 ensuing such that the specification of a viewing task 33 is not necessary. If a user is not satisfied with the resulting modified image or would like, for example, to have a different image modification displayed for a different diagnostic purpose, they may specify through an operating device 55 a corresponding viewing task or a desired ideal image impression class for the entire image or for segments of the image.

The method described may be implemented by a computer program that may be loaded into a memory 52 of the processing device 51. The process acts may be run by a processor 53. The computer program may be provided on an electronically readable data carrier, for example, a CD ROM, a DVD, a hard drive, a USB stick, or suchlike.

Although the disclosure has been illustrated and described in greater detail by the exemplary embodiments, the disclosure is not restricted by the disclosed examples and other variations may be derived herefrom by the person skilled in the art without departing from the scope of protection of the disclosure. It is therefore intended that the foregoing description be regarded as illustrative rather than limiting, and that it be understood that all equivalents and/or combinations of embodiments are intended to be included in this description.

It is to be understood that the elements and features recited in the appended claims may be combined in different ways to produce new claims that likewise fall within the scope of the present disclosure. Thus, whereas the dependent claims appended below depend from only a single independent or dependent claim, it is to be understood that these dependent claims may, alternatively, be made to depend in the alternative from any preceding or following claim, whether independent or dependent, and that such new combinations are to be understood as forming a part of the present specification.

The invention claimed is:

1. A method for adapting an image impression of an image, the method comprising:
    providing an image or input data from which the image is acquired;
    specifying an ideal image impression class for the image and/or for at least one image segment of the image that has been specified directly or by specifying at least one segment type, wherein a connection between image data in the image and/or in the respective image segment and an assigned image impression class is specified by a classification algorithm; and
    modifying the image or the input data, by a modification algorithm, in order to adapt the image impression class assigned to resulting modified image data pertaining to the image or pertaining to the respective image segment to match the respective ideal image impression class, wherein at least one modification parameter of the modification algorithm is specified or becomes specified as a function of the classification algorithm.

2. The method of claim 1, wherein the image is acquired in a context of medical imaging.

3. The method of claim 1, wherein the modification parameter is determined or becomes determined by machine learning.

4. The method of claim 1, wherein at least one classification parameter of the classification algorithm and the modification parameter are determined or become determined together by machine learning.

5. The method of claim 4, wherein, in a context of the machine learning, a learning algorithm tries at a same time or alternately to select the modification parameter such that when the classification algorithm is applied to a resulting image, which is acquired by applying the modification algorithm to an input image, or to the image segment of the resulting image that has been specified directly or by specifying the at least one segment type, a specified ideal image impression class is determined, and
    wherein the learning algorithm tries to select the classification parameter such that when the classification algorithm is applied to the resulting image or to the at least one image segment of the resulting image and to the input image or to the image segment of the input image that is assigned to the image segment of the resulting image, a same image impression class is determined.

6. The method of claim 1, wherein the image or the input data is or are acquired from original data by a processing algorithm, which is dependent on at least one processing parameter, and
wherein the image impression class of the image, the respective image segment, the segment type, or a combination thereof is dependent on the at least one processing parameter.

7. The method of claim 6, wherein the processing algorithm comprises a reconstruction algorithm for reconstructing three-dimensional volume data from two-dimensional original data, wherein the reconstruction algorithm depends on a processing parameter of the at least one processing parameter and/or wherein the image or the input data are two-dimensional image data generated by a mapping algorithm from the three-dimensional volume data, wherein the mapping algorithm is dependent on a processing parameter of the at least one processing parameter.

8. The method of claim 7, wherein the two-dimensional original data is X-ray images.

9. The method of claim 1, wherein different ideal image impression classes are specified for different image segments and/or different segment types.

10. The method of claim 1, wherein the ideal image impression class, the at least one image segment, the at least one segment type for which the ideal image impression class is specified, or a combination thereof is specified as a function of one or more of: a user input by a user, user information identifying the user, the image, the input data, original data, additional information relating to imaging of the image, or a patient shown in the image.

11. The method of claim 1, wherein specification of one or more of: the ideal image impression class, the at least one image segment, a segment type for which the ideal image impression class is specified, a specification of ideal image impressions configured to be selected by a user or recommended to the user, image segments, segment types for which ideal image impressions are selectable or recommended or specified ensues by a specifying algorithm, which is or becomes parameterized by machine learning.

12. The method of claim 1, wherein the modification algorithm is configured to automatically specify image segments and/or segment types and ideal image impression classes that have been assigned in each case, as a function of a viewing task that has been specified for the image.

13. The method of claim 1, wherein the image or the modified image data are shown for a user,
wherein at least one image region is highlighted, which includes a feature, a representation of which depends on an image impression classification of the image or at least of one segment of the image or on a viewing task that has been specified for the image.

14. The method of claim 1, wherein the image is acquired by a superimposed view from source images that describe the input data, and
wherein the modification algorithm processes the source images as the input data.

15. The method of claim 14, wherein the image is acquired by subtraction.

16. A processing device for processing images, the processing device comprising:
a processor configured to:
provide an image or input data from which the image is acquired;
specify a respective ideal image impression class for the image and/or for at least one image segment of the image that has been specified directly or by specifying at least one segment type, wherein a connection between image data in the image and/or in the respective image segment and an assigned image impression class is specified by a classification algorithm; and
modify the image or the input data, by a modification algorithm, in order to adapt the image impression class assigned to resulting modified image data pertaining to the image or pertaining to the respective image segment to match the respective ideal image impression class, wherein at least one modification parameter of the modification algorithm is specified or becomes specified as a function of the classification algorithm.

17. A non-transitory electronically readable data carrier comprising at least one computer program configured to, when executed on the electronically readable data carrier, cause a processing device to:
provide an image or input data from which the image is acquired;
specify a respective ideal image impression class for the image and/or for at least one image segment of the image that has been specified directly or by specifying at least one segment type, wherein a connection between image data in the image and/or in the respective image segment and an assigned image impression class is specified by a classification algorithm; and
modify the image or the input data, by a modification algorithm, in order to adapt the image impression class assigned to resulting modified image data pertaining to the image or pertaining to the respective image segment to match the respective ideal image impression class, wherein at least one modification parameter of the modification algorithm is specified or becomes specified as a function of the classification algorithm.

* * * * *